US012690812B2

(12) United States Patent (10) Patent No.: US 12,690,812 B2
Kusano et al. (45) Date of Patent: Jul. 28, 2026

(54) BODY CONDITION ESTIMATION SYSTEM AND SHOE

(71) Applicant: ASICS CORPORATION, Kobe (JP)

(72) Inventors: Ken Kusano, Kobe (JP); Takashi Inomata, Kobe (JP)

(73) Assignee: ASICS CORPORATION, Kobe (JP)

( * ) Notice: Subject to any disclaimer, the term of this patent is extended or adjusted under 35 U.S.C. 154(b) by 331 days.

(21) Appl. No.: 18/553,830

(22) PCT Filed: Apr. 20, 2021

(86) PCT No.: PCT/JP2021/016087

§ 371 (c)(1),
(2) Date: Oct. 3, 2023

(87) PCT Pub. No.: WO2022/224361

PCT Pub. Date: Oct. 27, 2022

(65) Prior Publication Data

US 2024/0180488 A1 Jun. 6, 2024

(51) Int. Cl.
*A61B 5/00* (2006.01)
*A43B 3/44* (2022.01)
(Continued)

(52) U.S. Cl.
CPC .............. *A61B 5/6807* (2013.01); *A43B 7/00* (2013.01); *A61B 5/112* (2013.01); *A61B 5/1121* (2013.01); *A61B 5/7278* (2013.01); *G01C 9/02* (2013.01)

(58) Field of Classification Search
CPC ..... A61B 5/6807; A61B 5/112; A61B 5/1121; A61B 5/7278; A61B 5/0022;
(Continued)

(56) References Cited

U.S. PATENT DOCUMENTS 5,724,265 A 3/1998 Hutchings
5,955,667 A 9/1999 Fyfe
(Continued)

FOREIGN PATENT DOCUMENTS

EP 3626169 A1 3/2020
JP 2014-504943 A 2/2014
(Continued)

OTHER PUBLICATIONS

The extended European search report issued by the European Patent Office on Apr. 3, 2024, which corresponds to European Patent Application No. 21937857.7-1015 and is related to U.S. Appl. No. 18/553,830.
(Continued)

*Primary Examiner* — Justin Xu
(74) *Attorney, Agent, or Firm* — Studebaker Brackett PLLC

(57) ABSTRACT
A body state estimation system includes a sensor module that detects an inclination around a certain axis of a shoe, and an estimation unit that estimates an inclination state of the body of a wearer of the shoe based on a detection result from the sensor module. The estimation unit estimates, for example, a heel valgus angle, an ankle dorsiflexion angle, and a knee flexion angle of the wearer, using a regression model.

18 Claims, 5 Drawing Sheets

(51) Int. Cl.

| | | |
|---|---|---|
| *A43B 3/48* | (2022.01) |
| *A43B 7/00* | (2006.01) |
| *A61B 5/107* | (2006.01) |
| *A61B 5/11* | (2006.01) |
| *G01C 9/02* | (2006.01) |

(58) Field of Classification Search

CPC ....... A61B 5/1071; A61B 5/4561; A43B 7/00; A43B 3/48; A43B 3/44; G01C 9/02

See application file for complete search history.

(56) References Cited

U.S. PATENT DOCUMENTS

| | | | | |
|---|---|---|---|---|
| 6,836,744 | B1 | 12/2004 | Asphahani et al. | |
| 2006/0213090 | A1 | 9/2006 | Nole | |
| 2008/0146968 | A1 | 6/2008 | Hanawaka et al. | |
| 2010/0094174 | A1* | 4/2010 | Choi .................... | A61B 5/1127 600/587 |
| 2011/0140897 | A1 | 6/2011 | Purks et al. | |
| 2013/0041617 | A1 | 2/2013 | Pease et al. | |
| 2019/0150793 | A1* | 5/2019 | Barth .................... | G06V 40/25 |

FOREIGN PATENT DOCUMENTS

| | | | |
|---|---|---|---|
| JP | 2018-038752 A | 3/2018 |
| KR | 10-2015-0117716 A | 10/2015 |
| WO | 2019/175899 A1 | 9/2019 |

OTHER PUBLICATIONS

International Search Report issued in PCT/JP2021/016087; mailed Jul. 20, 2021.

International Preliminary Report on Patentability (Chapter I) and Written Opinion of the International Searching Authority issued in PCT/JP2021/016087; issued Oct. 24, 2023.

Huang et al.; "Novel Foot Progression Angle Algorithm Estimation via Foot-Worn, Magneto-Inertial Sensing"; IEEE Transactions on Biomedical Engineering; Jan. 29, 2016; pp. 1-8; vol. 63, No. 11; IEEE; DOI: 10.1109/ TBME.2016.2523512; URL: https://ieeexplore.ieee.org/document/7395351.

An Office Action; mailed by the China National Intellectual Property Administration of the People's Republic of China on Apr. 8, 2026, which corresponds to Chinese Patent Application No. 202180097225.1 and is related to U.S. Appl. No. 18/553,830.

* cited by examiner

ELAPSED TIME

BODY CONDITION ESTIMATION SYSTEM AND SHOE

BACKGROUND

1. Technical Field

The present disclosure relates to a body state estimation system and a shoe.

2. Description of the Related Art

In recent years, with the spread of health consciousness, the number of people who perform exercise, such as running and walking, has been increasing. Performing such exercises properly can help maintenance of good health. On the other hand, since these exercises are movements that repeatedly apply a load to the same body part over a long period of time, it is important to adopt an appropriate exercise form to prevent injuries and other troubles. It is known that an analysis device such as a motion capture device is used in order to obtain an appropriate form. However, since the analysis device such as a motion capture device requires large-scale equipment, there is a certain need for a technology that enables understanding of body states more easily.

For example, Patent Literature 1 describes acquiring acceleration data of a lumbar region, which is the core part of the body during exercise, and estimating the load on the knee joints from the acquired data.

PATENT LITERATURE

Patent Literature 1: Japanese Unexamined Patent Application Publication No. 2018-038752

SUMMARY

A purpose of the present disclosure is to provide a body state estimation system that satisfies the abovementioned need using a method different from that of Patent Literature 1, and a shoe equipped with such a system.

According to one aspect of the present disclosure, there are provided a detector that detects an inclination around a certain axis of a shoe, and an estimation unit that estimates an inclination state of the body of a wearer of the shoe based on a detection result from the detector.

DESCRIPTION OF EMBODIMENTS

Figure 1:
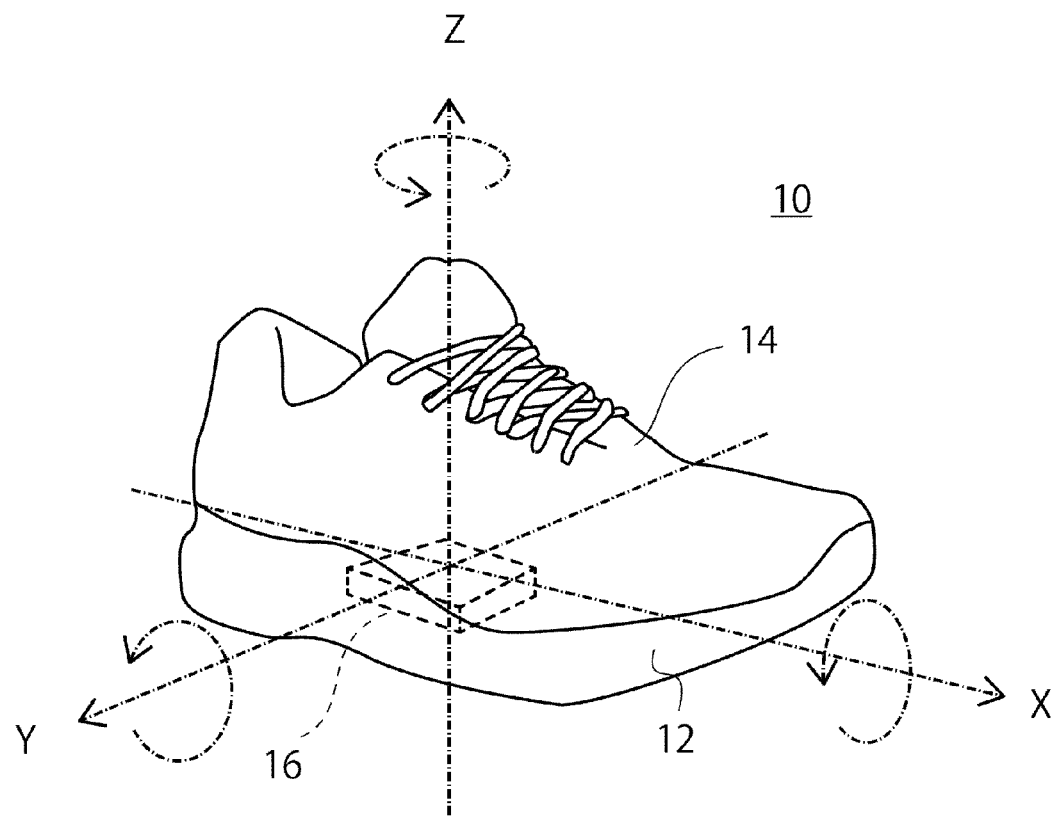
FIG. 1 is a schematic perspective view of a shoe according to an embodiment.

FIG. 1 is a schematic perspective view of a shoe according to an embodiment. As illustrated in FIG. 1, a shoe 10 is a so-called running shoe and includes a sole 12 and an upper 14. The sole 12 includes therein a sensor module 16 as a detector. The sensor module 16 is constituted by a 6-axis inertial sensor of MEMS structure that detects and outputs the acceleration in each axial direction and the angular velocity around each axis, in a three-dimensional Cartesian coordinate system constituted by an X-axis, a Y-axis, and a Z-axis. As the detector, a sensor other than a 6-axis inertial sensor may also be used. Also, although the sensor module 16 is built into a midfoot portion of the sole 12 in the embodiment, the position of the sensor module 16 is not limited thereto. For example, using an attachment or the like, the sensor module 16 may be attached to a shoelace or an outer surface of the shoe 10, such as the upper 14.

The X-axis of the three-dimensional Cartesian coordinate system extends from the heel side toward the toe side in a horizontal plane. The angular velocity around the X-axis is measured based on the premise that, when a shoe for the right foot is viewed from the front, the counterclockwise direction is the positive direction. The Y-axis extends from the medial side toward the lateral side in the same horizontal plane as for the X-axis. The angular velocity around the Y-axis is measured based on the premise that, when the shoe is viewed from the lateral side, the counterclockwise direction is the positive direction. The Z-axis is perpendicular to the horizontal plane and extends from the sole 12 side toward the upper 14 side. The angular velocity around the Z-axis is measured based on the premise that, when the shoe is viewed from the top, the counterclockwise direction is the positive direction.

Figure 2:
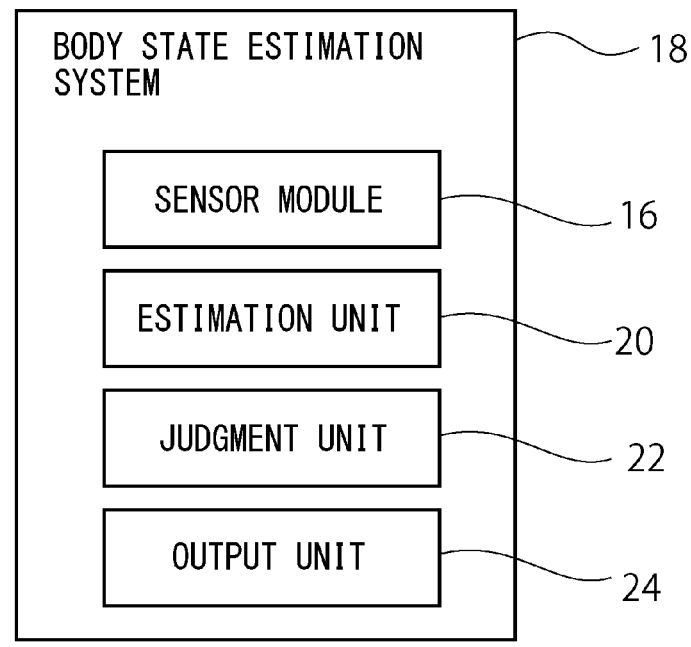
FIG. 2 is a block diagram of a body state estimation system mounted on the shoe.

FIG. 2 is a block diagram of a body state estimation system. As shown in FIG. 2, a body state estimation system 18 includes, besides the sensor module 16, an estimation unit 20, a judgment unit 22, and an output unit 24. The estimation unit 20 and the judgment unit 22 are conceptual and each represent a function actually implemented by executing a program in an appropriate calculation unit. Therefore, the estimation unit 20 and the judgment unit 22 need not necessarily be provided in a distinguishable manner.

The estimation unit 20 estimates inclination states of the body of the wearer of the shoe 10, based on the detection results from the sensor module 16. The body inclination states mean inclination states of various parts of the wearer, particularly inclination states of various parts of the wearer's lower body. The estimation unit 20 estimates inclination states other than inclination states that can be detected by the mounted sensor module 16. The inclination states other than inclination states that can be detected by the sensor module 16 mean inclination states that cannot be directly measured by the mounted sensor module 16, inclination states that can be directly measured theoretically but cannot be obtained as sufficient results with the detection performance of the sensor module 16, or inclination states of which direct measurement is difficult or impossible. The estimation unit 20 records an angular change in each axial direction and around each axis over time and estimates a body inclination state using the recorded contents and a predetermined regression equation. The body inclination states estimated by the estimation unit 20 include, for example, the heel varus/valgus angle, the ankle plantar/dorsiflexion angle, and the knee flexion/extension angle.

Although details will be described later, when the estimation unit 20 performs estimation without using a total of six detection results of acceleration in the X-axis, Y-axis, and Z-axis directions and angular velocities around the X-axis, Y-axis, and Z-axis, the number of detection axes of the sensor module 16 may be reduced as necessary, for example a 4-axis inertial sensor may be used.

The judgment unit 22 judges the gait of the wearer based on the estimation results from the estimation unit 20. The gait of the wearer means the wearer's posture during walking or running. Based on the angle, orientation, and the like of a predetermined specific part of the wearer's body, the judgment unit 22 estimates the posture of the part and thus the posture of the wearer's entire body or entire lower body. For example, when the estimation unit 20 estimates, as the body inclination states, the heel varus/valgus angle, the ankle plantar/dorsiflexion angle, and the knee flexion/extension angle, the judgment unit 22 judges whether the wearer's gait is appropriate based on each of the angles and a change over time thereof. As an example, the judgment unit 22 may have a threshold for each of angles that can be estimated by the estimation unit 20, and, when one of the angles exceeds its threshold, the judgment unit 22 can judge that the gait is inappropriate. In this case, the judgment unit 22 may output the judgment result via the output unit 24 to the wearer or an analyst.

Besides the example described above, the judgment by the judgment unit 22 may also be made by scoring and evaluating the degree of appropriateness of each angle.

The output unit 24 outputs the estimation results of the estimation unit 20 and/or the judgment result of the judgment unit 22 to the outside of the body state estimation system. As the output unit 24, a wireless communication system, such as Bluetooth (registered trademark) or a wireless LAN, may be used, for example.

The body state estimation system 18 may be implemented by causing hardware integrally built into the shoe 10 to function by means of software or may be implemented by connecting the shoe 10 and an external device by wired or wireless means and causing multiple pieces of hardware to function by means of software. When the body state estimation system is implemented by the shoe 10 and an external device, the sensor module 16 and an output unit, which transmits the detection results of the sensor module 16 to the external device, are built into the shoe 10. In other words, any hardware configuration may be adopted as long as at least the sensor module 16 of the body state estimation system 18 is built into the shoe 10.

In the following, the functions of the shoe according to the embodiment will be described.

While the wearer is wearing the shoe 10, the estimation unit 20 periodically acquires, from the sensor module 16, the detection results at rest and/or during walking (including running). Using the detection results thus acquired and a predetermined regression equation, the estimation unit 20 calculates a body inclination state. The calculation result of the estimation unit 20 is supplied as an estimation result to the output unit 24. The output unit 24 transmits the estimation result to a terminal used by the wearer or an analyst, for example. This allows the wearer or analyst to view the estimation result.

There will now be described specific functions of the estimation unit 20. The estimation of an angle described below is performed by the estimation unit 20 based on a command from a predetermined program.

In the following, the heel varus/valgus angle, ankle plantar/dorsiflexion angle, and knee flexion/extension angle are employed as examples of the body inclination states, and estimation methods therefor will be specifically described. The estimation unit 20 may be configured to estimate all of the multiple types of angles or may be configured to estimate only one or some of the types.

Estimation of Heel Valgus Angle

Figure 3:
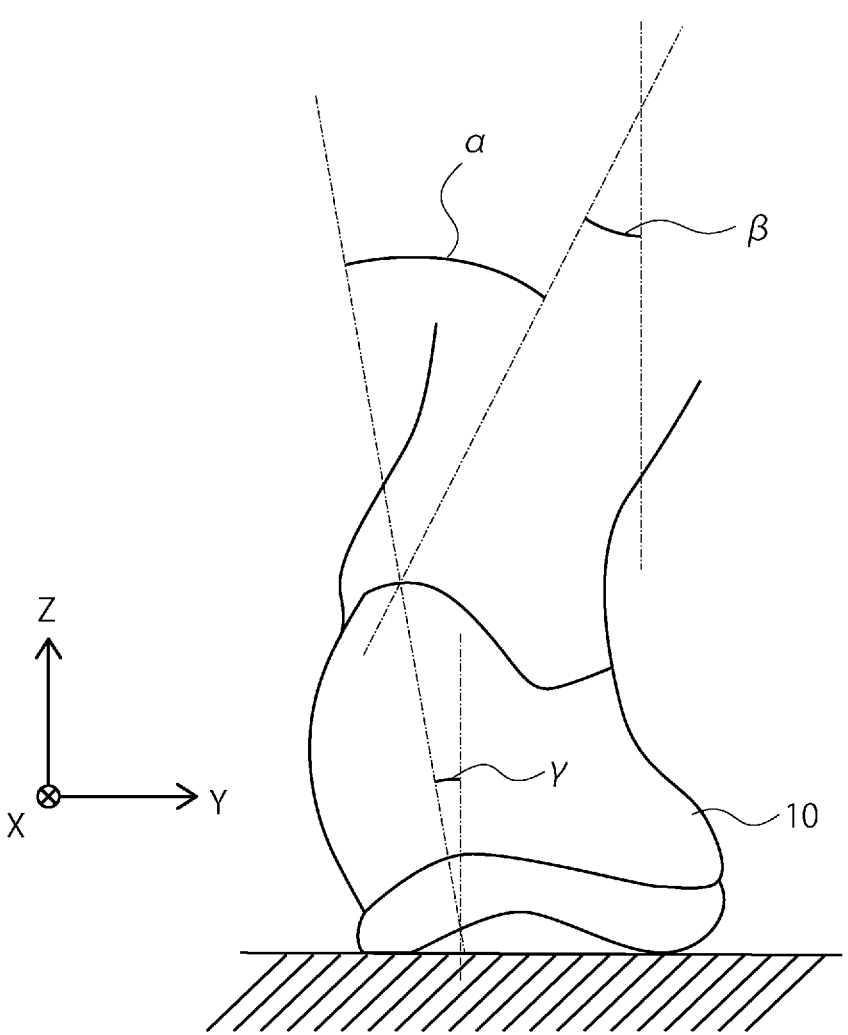
FIG. 3 is a schematic diagram of a foot.

FIG. 3 is a schematic diagram of a foot, viewed from the back side of the wearer. As shown in FIG. 3, a heel valgus angle α is an angle between a lower leg inclination angle β and a calcaneal valgus angle γ. The lower leg inclination angle β is an angle made by a lower leg on the medial side with respect to the Z-axis when the wearer is viewed from the back. The calcaneal valgus angle γ is an angle made by the calcaneus on the medial side with respect to the Z-axis when the wearer is viewed from the back. The heel valgus angle α is indicated by a negative value around the Y-axis. A state in which the absolute value of the heel valgus angle α is large is known as so-called overpronation, which is one of the causes of ankle injury for wearers. By enabling detection of changes in the heel valgus angle α or the peak value of the heel valgus angle α, the wearers can work on improving their forms, for example, to prevent overpronation.

Figure 4:
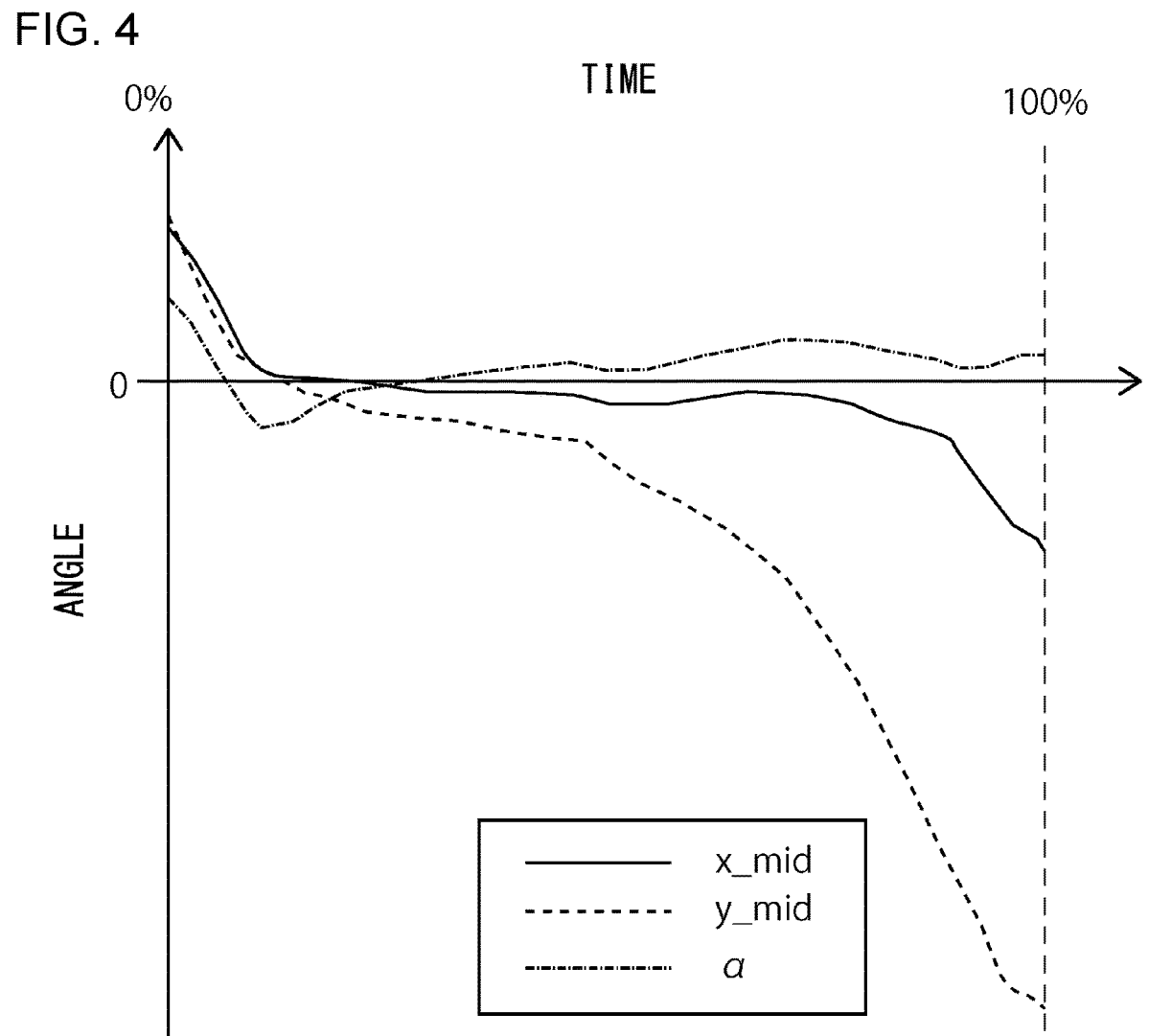
FIG. 4 is a graph that shows a change over time of the heel varus/valgus angle during running.

FIG. 4 is a graph that shows a change over time of the heel varus/valgus angle during running. In FIG. 4, the X-axis represents the elapsed time, and the Y-axis represents the change in angle. The X-axis represents the elapsed time as a value between 0 and 100%, with 0% indicating the start of a stance phase and 100% indicating the end of the stance phase. The angle on the Y-axis is indicated to be positive or negative according to the three-dimensional Cartesian coordinate system shown in FIG. 1. With regard to the value of the heel valgus angle α, the side where the valgus angle increases, i.e., the side where the lower leg is inclined outward of the body with respect to the heel, is defined to be negative. Also, when the usefulness of the embodiment is explained, the estimation by the estimation unit 20 may be described with reference to the results of tests conducted by the inventors and others, for the sake of convenience. However, the description regarding the test results is provided only to facilitate understanding of the processing performed in the estimation unit 20 and should not be referred to in construing the scope of the present disclosure.

The change over time of the angle around the X-axis and the change over time of the angle around the Y-axis are values that can be obtained directly from the detection results of the sensor module 16. Using these values and a regression equation, the estimation unit 20 calculates the heel valgus angle α.

First, the running states of people of various genders, ages, and weights were measured with a motion capture system. At this time, markers were attached to a heel portion and a lower leg portion so that the lower leg inclination angle β and the calcaneal valgus angle γ could be detected by the motion capture system. Thereafter, heel (calcaneus) and lower leg (tibia) coordinate systems were defined based on a publicly-known method, and the rotation angle of the calcaneus coordinate system with respect to the tibia coordinate system in a running state was calculated. At the time, the rotation angle around the Y-axis was defined as the heel varus/valgus angle. Also, a marker was attached to the midfoot portion of the shoe, and, among the relative angles between the coordinate system defined from the marker in the midfoot portion and the fixed coordinate system, the angle around the X-axis obtained from the sensor module 16 was defined as an angle x_mid, and the angle around the Y-axis obtained from the sensor module 16 was defined as an angle y_mid. Accordingly, a regression model for estimating the heel valgus angle α from the angle x_mid and the angle y_mid was constructed. In constructing the regression model, the angle x_mid and the angle y_mid at 0%, 5%, and 10% in a stance phase were used as the explanatory variables. In the regression model, a local minimum value of the heel valgus angle α was set as the objective variable. Although the regression model naturally varies depending on the running test conditions, as one of regression models obtained as the results of running tests conducted by the inventors and others, α=−1.980−0.424×x_mid0%+0.126y_mid10% was obtained. Here, x_mid0% is the value of x at 0% in the stance phase, and y_mid10% is the value of y at 10% in the stance phase.

As is evident from FIG. 4, the point at which the angle x_mid and the angle y_mid are 0 degrees in the stance phase indicates the moment when the entire sole comes into contact with the ground. Immediately thereafter, the heel valgus angle α shows its minimum value. Since the minimum value (peak value) of the heel valgus angle α is an important value for verification regarding overpronation, a regression model for estimating the heel valgus angle α is useful. The inventors and others created a regression model for estimating the peak value of the heel valgus angle α using linear regression analysis, and the coefficient of determination for actual running test results was 0.888.

Thus, the estimation unit 20 can estimate the heel valgus angle α, which cannot be directly measured by the sensor module 16, based on the detection obtained from the sensor module 16.

Estimation of Ankle Plantar/Dorsiflexion Angle

As with the heel varus/valgus angle, the ankle plantar/dorsiflexion angle can also be calculated from the angle x_mid as the angle around the X-axis and the angle y_mid as the angle around the Y-axis.

Figure 5:
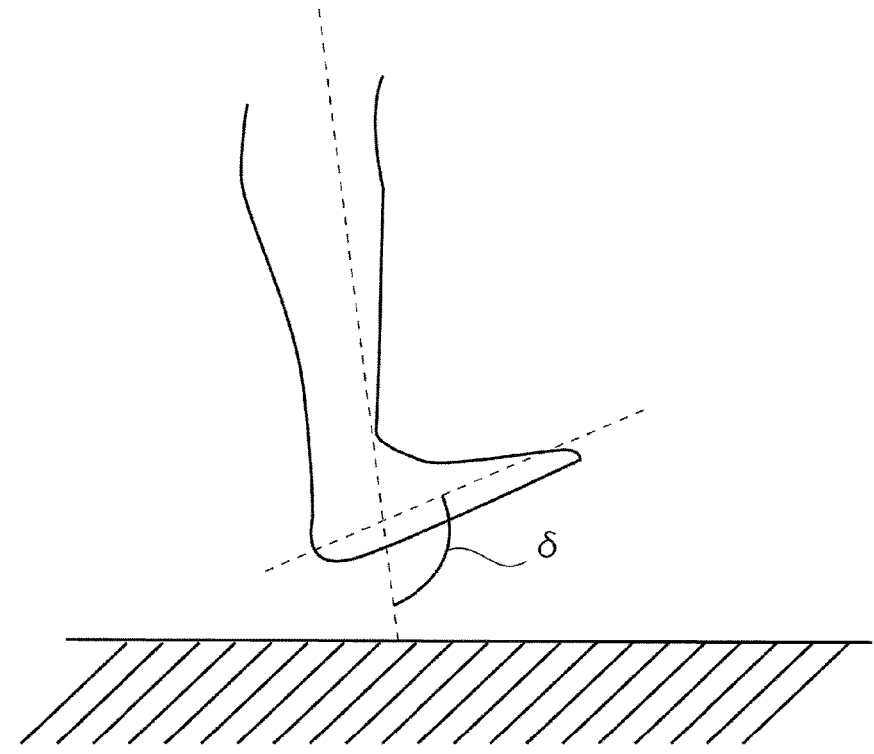
FIG. 5 is a schematic diagram of a foot.

FIG. 5 is a schematic diagram of a foot, viewed from a side of the wearer. As shown in FIG. 5, an ankle dorsiflexion angle δ is an angle between the sole and the lower leg in side view. As with the heel valgus angle α, the ankle dorsiflexion angle δ can also be estimated based on a regression model constructed with the angle x_mid and the angle y_mid.

Figure 6:
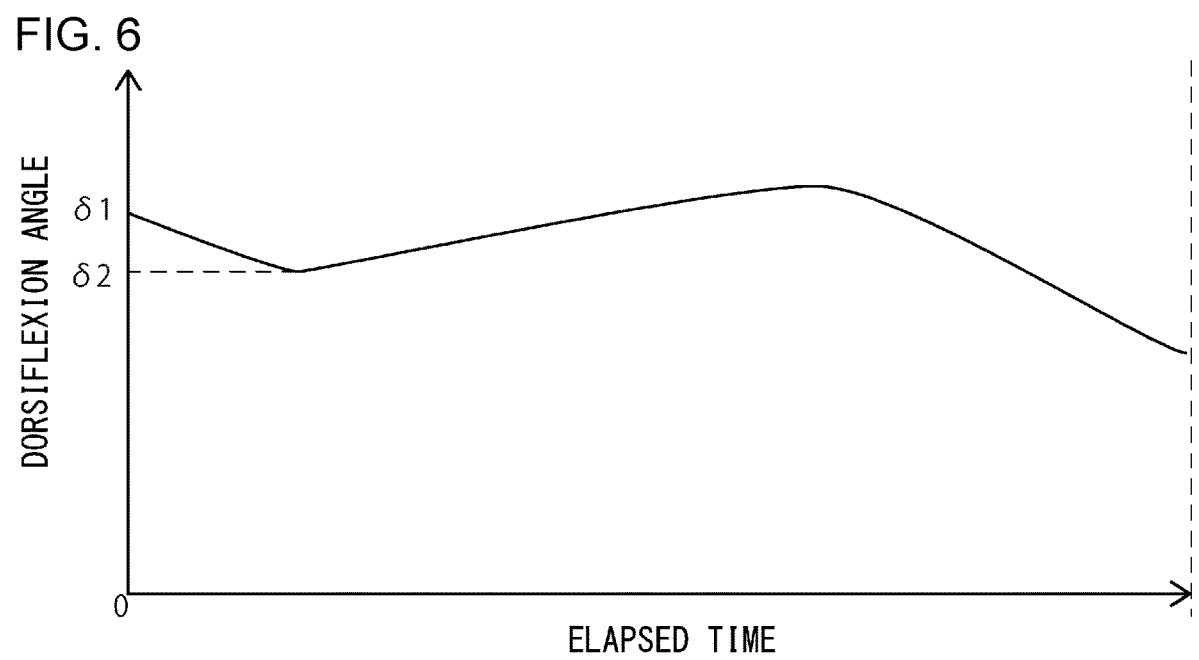
FIG. 6 is a graph that shows a change over time of the ankle plantar/dorsiflexion angle during running.

FIG. 6 is a graph that shows a change over time of the ankle plantar/dorsiflexion angle during running. The X-axis represents the time from when one foot comes into contact with the ground until the one foot leaves the ground during running. The Y-axis represents the ankle plantar/dorsiflexion angle, i.e., the angle between the lower leg and the sole. As shown in FIG. 6, in general, the ankle dorsiflexion angle δ is maximum at the time of ground contact. Thereafter, the ankle dorsiflexion angle δ decreases once and then increases again, through a local minimum. Since the load on the ankle is greater at the time of ground contact and at the local minimum, it is useful to obtain the ankle dorsiflexion angle δ at these points. In constructing the regression model, the angle x_mid and the angle y_mid were used as the explanatory variables. In the regression model, the ankle dorsiflexion angle δ at the time of ground contact or the local minimum value of the ankle dorsiflexion angle δ was set as the objective variable. As described previously, although the regression model varies depending on the running test conditions, as the regression models obtained as the results of running tests conducted by the inventors and others, δ1, the ankle dorsiflexion angle at the time of ground contact, = 90.589+0.319x_mid5%+0.545y_mid5%, and Ω, the local minimum value of the ankle dorsiflexion angle, =84.066−0.587x_mid10%+1.135y_mid15% were obtained.

Thus, the estimation unit 20 can estimate the ankle dorsiflexion angle δ, which cannot be directly measured by the sensor module 16, based on the detection obtained from the sensor module 16.

Estimation of Knee Flexion/Extension Angle

Figure 7:
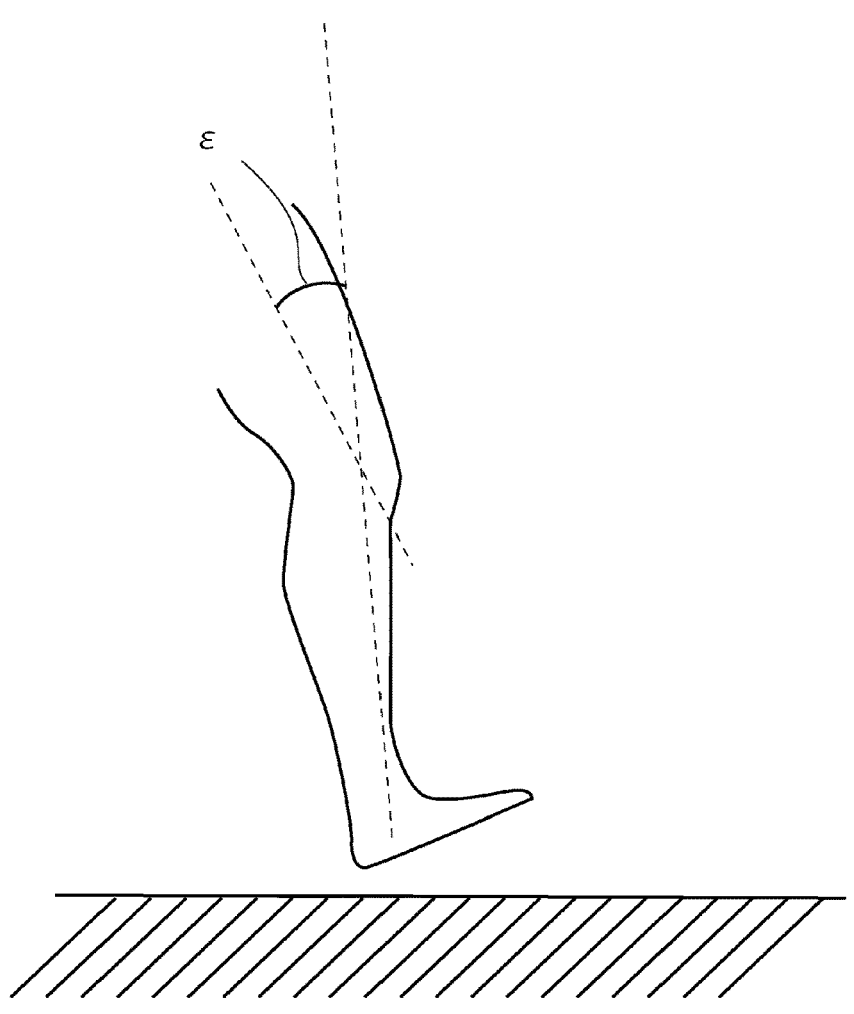
FIG. 7 is a schematic diagram of a lower leg.

As with the heel valgus angle, the knee flexion/extension angle can also be calculated from the angle x_mid as the angle around the X-axis and the angle y_mid as the angle around the Y-axis. FIG. 7 is a schematic diagram of a lower foot, viewed from a side of the wearer. As shown in FIG. 7, a knee flexion angle ε is an angle between the lower leg and the thigh in side view. As with the heel valgus angle α, the knee flexion angle ε can also be estimated based on a regression model constructed with the angle x_mid and the angle y_mid.

Figure 8:
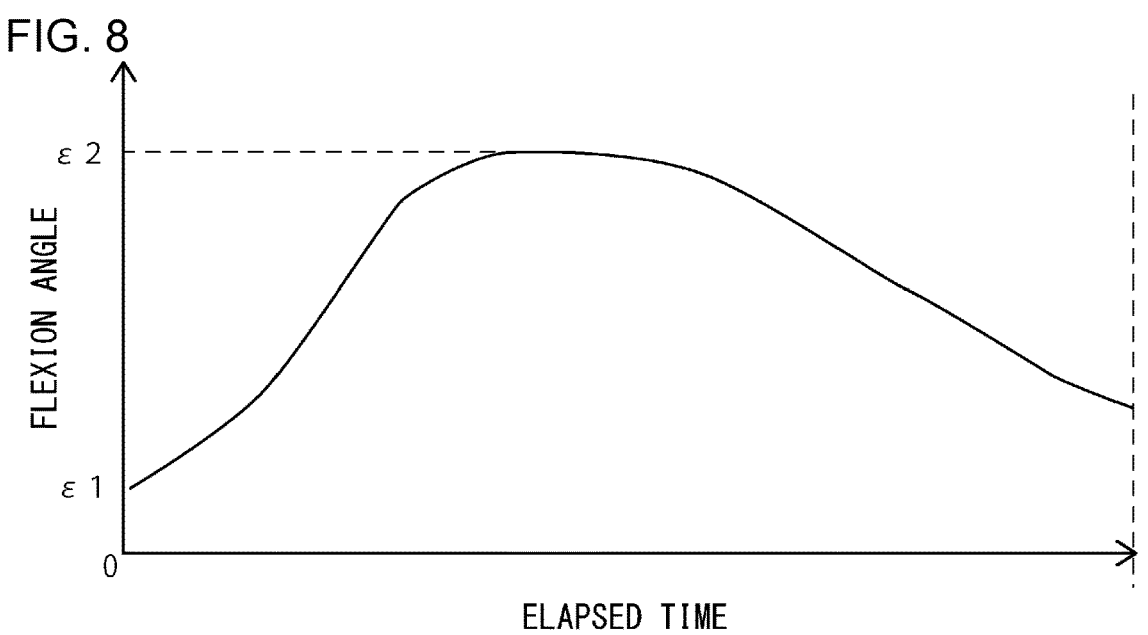
FIG. 8 is a graph that shows a change over time of the knee flexion/extension angle during running.

FIG. 8 is a graph that shows a change over time of the knee flexion/extension angle during running. The X-axis represents the elapsed time from when one foot comes into contact with the ground until the one foot leaves the ground during running. The Y-axis represents the knee flexion/extension angle, i.e., the angle between the lower leg and the thigh. As shown in FIG. 8, in general, the knee flexion angle ε is minimum at the time of ground contact. Thereafter, the knee flexion angle ε increases once and then decreases, through a local maximum. Since the load on the ankle is greater at the time of ground contact and at the local maximum, it is useful to obtain the knee flexion angle ε at these points. In constructing the regression model, the angle x_mid and the angle y_mid were used as the explanatory variables. In the regression model, the knee flexion angle ε at the time of ground contact or the local maximum value of the knee flexion angle ε was set as the objective variable. As described previously, although the regression model varies depending on the running test conditions, as the regression models obtained as the results of running tests conducted by the inventors and others, ε1, the knee flexion angle at the time of ground contact, =45.454+1.08x_mid0%+2.25x_mid15%+3.208x_mid15%, and ε2, the local maximum value of the knee flexion angle, =51.06+1.456x_mid15%−2.388x_mid20% were obtained.

Thus, the estimation unit 20 can estimate the knee flexion angle ε, which cannot be directly measured by the sensor module 16, based on the detection obtained from the sensor module 16.

As described above, the body state estimation system 18 is capable of estimating inclination states of the wearer's body. This allows the wearer to grasp points for improving the form, for example, based on the estimation results.

The present disclosure is not limited to the aforementioned embodiment, and modifications may be appropriately made to each configuration without departing from the spirit of the present disclosure.

Although the sensor module 16 is used as the detector in the aforementioned example, a terminal with an imaging function, such as a smartphone, may also be used as the detector. In this case, by capturing an image of a running state, the heel (calcaneus) and lower leg (tibia) coordinate systems of the person subject to analysis may be acquired, and the rotation angle of the calcaneus coordinate system with respect to the tibia coordinate system in the running state may be calculated.

Also, an application equipped with AI may be made to perform machine learning using, as a data set, a large number of detection results obtained by a sensor module or terminal, and a regression model may be constructed using the detection result learned model and the detection results.

What is claimed is:

1. A body state estimation system, comprising:
   a detector configured to detect an inclination around a predetermined axis of a shoe; and an estimation unit configured to estimate an inclination state of a wearer of the shoe, based on a detection result from the detector, wherein the inclination state is a heel valgus angle of the wearer of the shoe.

2. The body state estimation system according to claim 1, further comprising a judgment unit configured to judge a gait of a wearer based on an estimation result from the estimation unit.

3. The body state estimation system according to claim 2, wherein, based on a regression model set in advance to estimate the heel valgus angle, the estimation unit is configured to estimate the heel valgus angle of the wearer.

4. The body state estimation system according to claim 3, wherein the regression model is a model configured to estimate a peak value of the heel valgus angle.

5. The body state estimation system according to claim 1, wherein, based on a regression model set in advance and configured to estimate the heel valgus angle, the estimation unit is configured to estimate the heel valgus angle of the wearer.

6. The body state estimation system according to claim 5, wherein the regression model is a model configured to estimate a peak value of the heel valgus angle.

7. A shoe, comprising:

the body state estimation system according to claim 1; and an output unit configured to output a detection result from the detector to the estimation unit.

8. A body state estimation system, comprising:

a detector configured to detect an inclination around a predetermined axis of a shoe; and an estimation unit configured to estimate a heel valgus angle of a wearer of the shoe, based on the inclination around the predetermined axis of the shoe, wherein the heel valgus angle is an angle between a lower leg inclination angle of the wearer of the shoe and a calcaneal valgus angle of the wearer of the shoe, the lower leg inclination angle being an angle made by a lower leg on a medial side with respect to a Y-axis of the shoe extending from the medial side towards a lateral side when viewed from a back of the shoe and the calcaneal valgus angle being an angle made by a calcaneus on the medial side with respect to the Y-axis.

9. The body state estimation system according to claim 8, further comprising a judgment unit configured to judge a gait of a wearer based on the heel valgus angle.

10. The body state estimation system according to claim 9, wherein the estimation unit is configured to estimate the heel valgus angle using a regression model configured to estimate the heel valgus angle based on an angle of the inclination around the Y-axis of the shoe and an angle of the inclination around an X-axis of the shoe extending from a heel side towards a toe side in a horizontal plane that is the same horizontal plane for the Y-axis.

11. The body state estimation system according to claim 10, wherein the regression model is configured to estimate a peak value of the heel valgus angle, and the estimation unit is configured to estimate the heel valgus angle based on the peak value of the heel valgus angle.

12. The body state estimation system according to claim 8, wherein the estimation unit is configured to estimate the heel valgus angle using a regression model configured to estimate the heel valgus angle based on an angle of the inclination around the Y-axis of the shoe and an angle of the inclination around an X-axis of the shoe extending from a heel side towards a toe side in a horizontal plane that is the same horizontal plane for the Y-axis.

13. The body state estimation system according to claim 12, wherein the regression model is configured to estimate a peak value of the heel valgus angle, and the estimation unit is configured to estimate the heel valgus angle based on the peak value of the heel valgus angle.

14. A shoe, comprising:

the body state estimation system according to claim 8; and an output unit configured to output the heel valgus angle to an external terminal configured to display the heel valgus angle.

15. A body state estimation system, comprising:

a detector configured to detect an inclination around a predetermined axis of a shoe; and an estimation unit configured to estimate an inclination state of a wearer of the shoe, based on a detection result from the detector, wherein the inclination state is a heel valgus angle of the wearer of the shoe, based on a regression model set in advance and configured to estimate the heel valgus angle, the estimation unit is configured to estimate the heel valgus angle of the wearer, and the regression model is a model that uses, as explanatory variables, an angle around an axis extending from a heel side toward a toe side of the shoe and an angle around an axis extending from an medial side toward an lateral side of the shoe, each at a plurality of time points during a stance phase, and uses, as an objective variable, a peak value of the heel valgus angle.

16. A shoe, comprising:

the body state estimation system according to claim 15; and an output unit configured to output the heel valgus angle to an external terminal configured to display the heel valgus angle.

17. The body state estimation system according to claim 15, wherein the heel valgus angle is an angle between a lower leg inclination angle of the wearer of the shoe and a calcaneal valgus angle of the wearer of the shoe, the lower leg inclination angle being an angle made by a lower leg on a medial side with respect to a Y-axis of the shoe extending from the medial side towards a lateral side when viewed from a back of the shoe and the calcaneal valgus angle being an angle made by a calcaneus on the medial side with respect to the Y-axis.

18. A shoe, comprising:

the body state estimation system according to claim 17; and an output unit configured to output the heel valgus angle to an external terminal configured to display the heel valgus angle.

\* \* \* \* \*